United States Patent [19]

Kishita et al.

[11] Patent Number: 5,198,593

[45] Date of Patent: Mar. 30, 1993

[54] PROCESS FOR PURIFICATION OF ETHYLENE COMPOUND HAVING FLUORINE-CONTAINING ORGANIC GROUP

[75] Inventors: Hirofumi Kishita; Shinichi Sato; Hideki Fujii; Takashi Matsuda, all of Annaka, Japan

[73] Assignee: Shin-Etsu Chemical Co., Ltd., Tokyo, Japan

[21] Appl. No.: 858,211

[22] Filed: Mar. 26, 1992

[30] Foreign Application Priority Data

Mar. 26, 1991 [JP] Japan .................................. 3-086090

[51] Int. Cl.$^5$ ...................... C07C 17/38; B01J 19/12
[52] U.S. Cl. ..................... 570/177; 204/131; 204/157.92; 204/157.95; 204/158.21
[58] Field of Search ............... 570/177; 204/157.92, 204/157.95, 131, 158, 158.21

[56] References Cited

U.S. PATENT DOCUMENTS

| | | | |
|---|---|---|---|
| 4,004,993 | 1/1977 | Horner et al. | 204/131 |
| 4,775,450 | 10/1988 | Ajami | 204/131 |
| 5,000,830 | 3/1991 | Marchionni | 204/157.92 |
| 5,102,510 | 4/1992 | Darian | 204/157.92 |

FOREIGN PATENT DOCUMENTS

| | | | |
|---|---|---|---|
| 0151697 | 8/1985 | European Pat. Off. | |
| 0357328 | 3/1990 | European Pat. Off. | 570/177 |
| 4122196 | 1/1992 | Fed. Rep. of Germany | |
| 869273 | 5/1961 | United Kingdom | 570/177 |
| 1077363 | 7/1967 | United Kingdom | 570/177 |

OTHER PUBLICATIONS

Patent Abstracts of Japan, vol. 15, No. 445 (C-884), Nov. 13, 1991, & JP-A-3-190-826, N. Okada, et al., Aug. 20, 1991, "Method For Treating Fluorinated Product".

*Primary Examiner*—Werren B. Lone
*Attorney, Agent, or Firm*—Oblon, Spivak, McClelland, Maier & Neustadt

[57] ABSTRACT

A process for purifying an ethylene compound having a fluorine-containing organic group (fluorine-containing ethylene compound) by mixing the fluorine-containing ethylene compound with an alkali metal or alkaline earth metal reducing agent, and subjecting the resulting mixture to irradiation with ultraviolet radiation, followed by washing with water. The purification process ensures effective removal of iodides which are sources of molecular iodine, from the fluorine-containing ethylene compound.

6 Claims, No Drawings

PROCESS FOR PURIFICATION OF ETHYLENE COMPOUND HAVING FLUORINE-CONTAINING ORGANIC GROUP

BACKGROUND OF THE INVENTION

1. Field of the Invention

The present invention relates to a process for purifying an ethylene compound having a fluorine-containing organic group, and more particularly to a purification process by which iodine contained as impurity an ethylene compound having a fluorine-containing organic group can be removed effectively.

2. Description of the Prior Art

Ethylene compounds having a mono or bifuncitonal fluorine-substituted ethylenically unsaturated compound (hereinafter referred to as "fluorine-containing ethylene compounds") are capable of reaction with organosilicon compounds having Si-H bonds such as hydrosilane or hydrosiloxane (hydrosilylation reaction) in the presence of a platinum catalyst. Therefore, the fluorine-containing ethylene compounds are useful as compounds for introducing a fluorine-containing organic group into silane compounds, polysiloxanes, etc.

Such fluorine-containing ethylene compounds are, in general, synthesized according to the following reaction path:

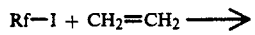

wherein Rf is a fluorine-containing organic group.

As is seen from the above reaction path, the fluorine-containing ethylene compounds contain iodides such as the starting material Rf-I and intermediate product. Rf-CH$_2$CH$_2$-I, as impurities. Where such a fluorine-containing ethylene compound is served to the aforementioned hydrosilylation reaction, the iodides contained as impurities in the ethylene compound generate molecular iodine during the reaction, and the molecular iodine acts as a catalyst poison. Consequently, the yield of the product obtained by the hydrosilylation reaction is low, and the product is colored in red due to the molecular iodine.

As a method of purifying the fluorine-containing ethylene compounds, there have been known a number of processes, for example, a process in which activated carbon is used to remove the impurities through adsorption, and a process in which a reducing agent is used to remove the impurities through reduction. These conventional processes are effective for removal of molecular iodine from the fluorine-containing ethylene compound, but are not effective in removing the iodides which are generation sources of the molecular iodine. Therefore, even where a fluorine-containing ethylene compound is served to the aforesaid hyirosilylation reaction after treated by such conventional purification process, the problems of yield and coloring of the product still remain unsolved.

SUMMARY OF THE INVENTION

It is accordingly an object of the present invention to provide a purification process by which a fluorine-containing ethylene compound free of iodides and molecular iodine can be obtained.

According to the present invention, there is provided a process for purification of an ethylene compound having a fluorine-containing organic group (fluorine-containing ethylene compound) which comprises the steps of:

(a) mixing the ethylene compound with at least one reducing agent selected from the group consisting of alkali metal reducing agents and alkaline earth metal reducing agents, and (b) irradiating the mixture obtained in step (a) with ultraviolet radiation.

In the process of the present invention, iodides contained as impurities in the fluorine-containing ethylene compound are, upon irradiation with ultraviolet radiation, decomposed to generate molecular iodine. The molecular iodine is reduced by the reducing agent into a water-soluble iodide, which is easily removed by washing with water.

DETAILED DESCRIPTION OF THE INVENTION

Fluorine-Containing Ethylene Compound

In the process according to the present invention, a fluorine-containing ethylene compound to be purified is one which is synthesized by using a fluorine-containing organic iodide having a perfluoroalkyl group, a perfluoroalkyl ether group or the like as a starting material. Namely, the fluorine-containing ethylene compound can be obtained by reacting the fluorine-containing organic iodide with ethylene, and permitting the resulting fluorine-containing organic ethyl iodide to be acted upon by an alkali metal hydroxide such as potassium hydroxide, etc. Such fluorine-containing ethylene compounds are not limited to monofunctional ones, and may be bifunctional. Typical, but not limitative, examples of the fluorine-containing ethylene compound include the compounds having the following formulas:

C$_2$F$_5$CH=CH$_2$,
C$_3$F$_7$CH=CH$_2$,
C$_4$F$_9$CH=CH$_2$,
C$_6$F$_{13}$CH=CH2,
C$_7$F$_{15}$CH=CH$_2$,
C$_8$F$_{17}$CH=CH$_2$,
C$_3$F$_7$O[CF(CF$_3$)CF$_2$O]$_n$CF(CF$_3$)CH=CH$_2$,
C$_3$F$_7$O[CF(CF$_3$)CF$_2$O]$_n$CF(CF$_3$)C-F$_2$OCF$_2$CF$_2$CH=CH$_2$,
CH$_2$=CHC$_6$F$_{12}$CH=CH$_2$,
CH$_2$=CHCF(CF$_3$)[OCF$_2$CF(CF$_3$)]$_m$OCF$_2$C-F$_2$O[CF(CF$_3$)CF$_2$O]$_n$CF(CF$_3$)CH =CH$_2$, wherein n is an integer of 0 or above, m is an integer of 0 or above, and n+m is an integer of 0 or above.

(a) Mixing of Reducing Agent

In the process of the present invention, the fluorine-containing ethylene compound is first mixed with a reducing agent. As the reducing agent, at least one compound selected from the group consisting of alkali metal reducing agents and alkaline earth metal reducing agents is used. The alkali metal reducing agents which can be used include, for example, alkali metal hydroxides such as sodium hydroxide, potassium hydroxide, etc., alkali metal carbonates such as sodium carbonate, potassium carbonate, etc., alkali metal thiosulfates such as sodium thiosulfate, and so on. The alkaline earth metal reducing agents usable include, for example, alkaline earth metal hydroxides such as calcium hydroxide, barium hydroxide, and so on.

The reducing agent is used for reduction of molecular iodine which is generated upon irradiation of the reactants with ultraviolet radiation. In general, the reducing agent is used preferably in an amount of from 0.1 to 50 parts by weight per 100 parts by weight of the fluorine-containing ethylene compound.

The mixing of the fluorine-containing ethylene compound with the reducing agent can be carried out by an arbitrary means. For example, the fluorine-containing ethylene compound may be mixed with a solid reducing agent used as it is. Alternatively, a solid reducing agent may be dissolved in water or be dissolved or dispersed in an organic solvent, followed by mixing the fluorine-containing ethylene compound with the aqueous solution or organic-solvent solution or dispersion of the reducing agent. Generally, it is preferable to use the reducing agent in the form of an aqueous solution.

Where the reducing agent is used as an aqueous solution or organic-solvent solution or dispersion, the concentration of the reducing agent is preferably 0.5% by weight or above. If the concentration is excessively low, sufficient reduction of molecular iodine may be impossible. The organic solvents usable as a solvent or dispersion medium for the reducing agent are those which do not absorb ultraviolet radiations. The usable organic solvents include, for example, alcohols such as methanol, ethanol, etc., glycols such as ethylene glycol, diethylene glycol, etc., ethers such as diethylene glycol dimethyl ether, diethyl ether, tetrahydrofuran, and so on. Of these organic solvents, preferred are alcohols such as methanol, ethanol, etc.

(b) Irradiation With Ultraviolet Radiation

In the process according to the present invention, the mixture of the fluorine-containing ethylene compound with the reducing agent is irradiated with ultraviolet radiation. By the irradiation with ultraviolet radiation, iodides contained as impurities in the fluorine-containing ethylene compound are decomposed to generate molecular iodine. The molecular iodine thus generated is immediately reduced by the reducing agent to a water-soluble iodide such as alkali iodide.

The ultraviolet radiation for irradiation therewith is preferably ultraviolet rays of a wavelength from 180 to 400 nm, for example. The irradiation with ultraviolet radiation is carried out until the iodides contained as impurities in the fluorine-containing ethylene compound are entirely decomposed; normally, an irradiation period of 30 minutes or above may be sufficient.

As a light source for the irradiation with ultraviolet radiation as described above, ordinary UV light sources may be used. Exposure systems having such light source include, for example, non-imaging exposure systems such as contact exposure systems, semi-contact exposure systems, proximity exposure systems, etc. and imaging exposure systems such as reflective projection exposure systems, refractive projection exposure systems, etc. More specific examples of the usable light sources include mercury vapor lamps such as low pressure mercury vapor lamps, high pressure mercury vapor lamps, extra-high pressure mercury vapor lamps, etc., ozone lamps, germicidal lamps, lamps for germicidal and health use, lamps for poultry-farming use, black-light fluorescent lamps, fluorescent lamps for copying use, fluorescent lamps for insect-catching use, and so on.

In the present invention it is essential that the irradiation with UV radiation be carried out in the presence of the reducing agent. For example, if the mixing of the fluorine-containing ethylene compound with the reducing agent is carried out after the irradiation with ultraviolet radiation, the intended effect is unattainable.

In the process according to the present invention, the irradiation with ultraviolet radiation in the presence of a reducing agent as described above causes the iodides contained as impurities to be converted through molecular iodine to a water-soluble iodide. By washing with water subsequent to the irradiation with ultraviolet radiation, therefore, it is possible to remove the iodine-containing impurities substantially completely.

Where a fluorine-containing ethylene compound having been subjected to the purification treatment as above is served to a hydrosilylation reaction, poisoning of catalyst does not occur and, therefore, the yield of the reaction product is extremely high. Furthermore, coloring of the reaction product by iodine is obviated effectively.

EXAMPLES

Example 1

(1) Perfluoro-n-butyl iodide and ethylene were reacted by supplying ethylene at a reaction temperature of from 50° to 80° C. and using azobisisobutyronitrile as a reaction initiator. Then, the resulting 3,3,4,4,5,5,6,6,6-fluorohexyl iodide was reacted with potassium hydroxide in methanol solvent at a temperature ranging from 5° to 20° C., to form perfluoro-n-butylethylene. The content of iodine in the perfluoro-n-butylethylene thus obtained was measured by potentiometric titration using silver nitrate, and found to be 254 ppm.

(2) A 300-ml flask equipped with a reflux condenser, a magnetic stirrer and a 100-W high pressure mercury vapor lamp was charged with 200 g of the perfluoro-n-butylethylene obtained in (1) above and with 100 g of a 3% by weight aqueous solution of sodium thiosulfate as a reducing agent. The resulting mixture in the flask was irradiated with ultraviolet radiation at room temperature for 5 hours with stirring. The solution resulting upon the treatment in the flask was separated into two layers, and the organic layer was then taken out and washed with water. The content of iodine in the solution thus obtained was measured by potentiometric titration using silver nitrate to be 1 ppm or below.

Then 150.0 g of the perfluoro-n-butylethylene deprived of iodine by the above treatment, 84.0 g of methyldichlorosilane and a catalytic amount of a platinum catalyst were placed in a pressure vessel. The mixture in the vessel was heated with stirring at 110° C. for 6 hours, thereby bringing the perfluoro-n-butylethylene into the hydrosilylation reaction. After the reaction was over, a colorless transparent reaction product was obtained in an amount of 232.0 g (yield: 98%). The iodine content of the perfluoro-n-butylethylene upon the iodine-removing treatment as well as the yield and the presence or absence of coloring of the hydrosilylation reaction product in Example 1 are set forth in Table 1 below.

Example 2

A treatment for removing iodine contained in perfluoro-n-butylethylene was carried out in the same manner as in Example 1, except that 100 g of a 5% by weight aqueous solution of sodium hydroxide was used as a reducing agent. Then, the content of iodine in the perfluoron-butylethylene thus treated was determined in the same manner as in Example 1, and found to be 1 ppm or below.

Subsequently, the perfluoro-n-butylethylene deprived of iodine as above was subjected to hydrosilylation reaction in the same manner as in Example 1. After the reaction was over, a colorless transparent reaction product was obtained in an amount of 231.7 g (yield: 97%). The iodine content as well as the yield and the presence or absence of coloring in Example 2 are set forth in Table 1.

Comparative Example 1

The perfluoro-n-butylethylene (200 g) as described in Example 1 (1) above was treated by mixing with 10 g of activated carbon for adsorbing iodine thereon. After the activated-carbon treatment, the content of iodine in the resultant perfluoro-n-butylethylene was measured in the same manner as in Example 1, and found to be 50 ppm.

Further, the perfluoro-n-butylethylene treated with activated carbon was subjected to hydrosilylation reaction in the same manner as in Example 1, to give 232.1 g of a red-colored reaction product (yield: 20%). The iodine content of the perfluoro-n-butylethylene upon the iodine-removing treatment as well as the yield and the presence or absence of coloring of the hydrosilylation reaction product in Comparative Example 1 are set forth in Table 1 below.

Comparative Example 2

The perfluoro-n-butylethylene (200 g) as described in Example 1 (1) above was treated by mixing with a reducing agent, 100 g of 5 wt. % aqueous sodium hydroxide solution for removal of iodine through reduction. The perfluoro-n-butylethylene thus treated with the reducing agent was subjected to iodine content measurement in the same manner as in Example 1. The iodine content was 152 ppm.

Subsequently, the perfluoro-n-butylethylene treated with the reducing agent as above was subjected to hydrosilylation reaction in the same manner as Example 1, to give 231.7 g of a red-colored reaction product (yield: 7%). The iodine content as well as the yield and the presence or absence of coloring in Comparative Example 2 are given in Table 1.

Comparative Example 3

The perfluoro-n-butylethylene (200 g) as described in Example 1 (1) above was irradiated with ultraviolet radiation for 5 hours to convert iodine in a combined form (i.e., iodine in iodides) into free iodine (i.e., molecular iodine), and then treated by mixing with a reducing agent, 100 g of 3 wt. % aqueous sodium thiosulfate solution, for removal of the free iodine through reduction. After the irradiation treatment and the reducing treatment, the content of iodine in the resultant perfluoro-n-butylethylene was measured in the same manner as in Example 1. The iodine content was 110 ppm.

Further, the perfluoro-n-butylethylene after the reducing-agent treatment was subjected to hydrosilylation reaction in the same manner as in Example 1, to give 232.1 g of a red-colored reaction product (yield: 5%). The iodine content as well as the yield and the presence or absence of coloring in Comparative Example 3 are set forth in Table 1.

TABLE 1

|  | Iodine content | Yield | Coloring |
| --- | --- | --- | --- |
| Example 1 | 1 ppm or below | 98% | absent |
| Example 2 | 1 ppm or below | 97% | absent |
| Comparative Example 1 | 50 ppm | 20% | present |
| Comparative Example 2 | 152 ppm | 7% | present |
| Comparative Example 3 | 110 ppm | 5% | present |

We claim:

1. A process for purification of a mono or bifunctional fluorine-substituted ethylenically unsaturated compounds which contains molecular iodine or an unsanctioned iodine, which comprises:
   (a) mixing said compound with at least one reducing agents selected from the group consisting of an alkali metal hydroxide, alkaline metal carbonate, alkaline metal thiosulfate, and alkaline earth metal hydroxide, and
   (b) irradiating the mixture obtained in step (a) with ultraviolet radiation in an amount sufficient to decompose any iodides present, and
   (c) removing any water-soluble iodides present by water washing of the mixture.

2. The process according to claim 1, wherein the reducing agent is used in an amount of from 0.1 to 50 parts by weight per 100 parts by weight of the mono or bifunctional fluorine-substituted ethylenically unsaturated compound.

3. The process of claim 1, wherein the reducing agent is used in the form of an aqueous solution.

4. The process according to claim 1, wherein the ultraviolet radiation comprises ultraviolet radiation of a wavelength of from 180 to 400 nm.

5. The process according to claim 1, wherein the step of irradiation with ultraviolet radiation is followed by washing with water.

6. The process according to claim 2, wherein the reducing agent is selected from the group consisting of NaOH, KOH, $Na_2CO_3$, $K_2CO_3$, $Na_2S_2O_3$, $Ca(OH)_2$ and $Ba(OH)_2$.

* * * * *